United States Patent [19]

Kato

[11] Patent Number: 5,200,975
[45] Date of Patent: Apr. 6, 1993

[54] FURNACE FOR VISCOELASTICITY MEASURING DEVICE WITH CONCENTRIC GAS COOLING SHIELD

[75] Inventor: Hidetaka Kato, Tokyo, Japan

[73] Assignee: Seiko Instruments Inc., Tokyo, Japan

[21] Appl. No.: 799,357

[22] Filed: Nov. 27, 1991

[30] Foreign Application Priority Data

Nov. 29, 1990 [JP] Japan .................. 2-130372[U]

[51] Int. Cl.⁵ .............................................. B01L 7/00
[52] U.S. Cl. ..................... 373/109; 73/863.11; 73/789; 374/45; 432/77; 432/202
[58] Field of Search ................ 373/109, 113; 73/863.11, 789, 760; 118/724, 725; 374/45, 50, 52, 53, 55-57, 5; 432/48, 81, 82, 77, 202, 225, 233

[56] References Cited

U.S. PATENT DOCUMENTS 4,967,601 11/1990 Teramoto ........................ 73/789

FOREIGN PATENT DOCUMENTS 1191605 4/1965 Fed. Rep. of Germany ........ 374/45
64-55821 3/1989 Japan .
1275280 12/1986 U.S.S.R. ............................. 374/50
1178687 1/1970 United Kingdom ............. 73/863.11
2131259 9/1982 United Kingdom .

Primary Examiner—Bruce A. Reynolds
Assistant Examiner—John A. Jeffery
Attorney, Agent, or Firm—Spensley Horn Jubas & Lubitz

[57] ABSTRACT

A double cylinder comprises an inside cylinder around which a heater wire is wound and a cylinder disposed outside thereof, and a furnace body filled an adiabatic material. Since cool air from a liquid vaporization type cooling device is passed through a gap between the outside and inside cylinders while cooling the outside of the inner cylinder around which the heater wire is wound, and is then ejected, no air current is produced inside the inner cylinder and, consequently, there is no temperature fluctuation at the thermocouple portion in the vicinity of the sample. As a result, linearity of a line indicative of a temperature rise is improved when the temperature is raised from low temperature.

8 Claims, 1 Drawing Sheet

FURNACE FOR VISCOELASTICITY MEASURING DEVICE WITH CONCENTRIC GAS COOLING SHIELD

BACKGROUND OF THE INVENTION

The present invention relates to an improvement in a dynamic viscoelasticity device for detecting interdependence between the viscoelastic property of a material and temperature, time, and frequency and the like, in order to improve stability in a temperature rise from a low temperature of −150° C. in a heating furnace for changing the temperature of a material.

Conventional heating furnaces used for raising temperature from a low temperature of −150° C. and for keeping the temperature constant, have a configuration as shown in FIG. 2. Specifically, an outer cylinder 3 in which a heater wire 2 is disposed, is fixed in an adiabatic portion 7 made of an adiabatic material and, further, there is a sample 12 which is attached to the inside thereof with an insertable probe 11. Cool air introduced by a hose 9 of a liquid nitrogen vaporization type cooling device which is not shown, is passed via a cool air introduction hole 4 through meshes 13 provided at a thrust portion of the outer cylinder 3 around which the heater wire 2 is wound, to be directly sprayed upon the sample.

The conventional device which directly applies cool air to a sample, has a problem that the linearity of a temperature rise from low temperature is adversely affected by temperature fluctuation at a thermocouple portion disposed in the vicinity of the sample which is caused by an air current produced inside the cylinder.

SUMMARY OF THE INVENTION

The present invention has been conceived to eliminate the above-mentioned problem and is mainly comprised of a double cylinder comprising an inside cylinder around which a heater wire is wound and a cylinder disposed ouside thereof, and a furnace body filled with an adiabatic material.

Since cool air fed in from a liquid nitrogen vaporization type cooling device is passed through a gap between the outside and inside cylinders while cooling the outside of the inner cylinder around which the heater wire is wound, and is then ejected, no air current is produced inside the inner cylinder and, consequently, there is no temperature fluctuation at the thermocouple portion in the vicinity of the sample. As a result, the linearity of a line indicative of a temperature rise is improved when the temperature is raised from low temperature.

DETAILED DESCRIPTION

Figure 1:
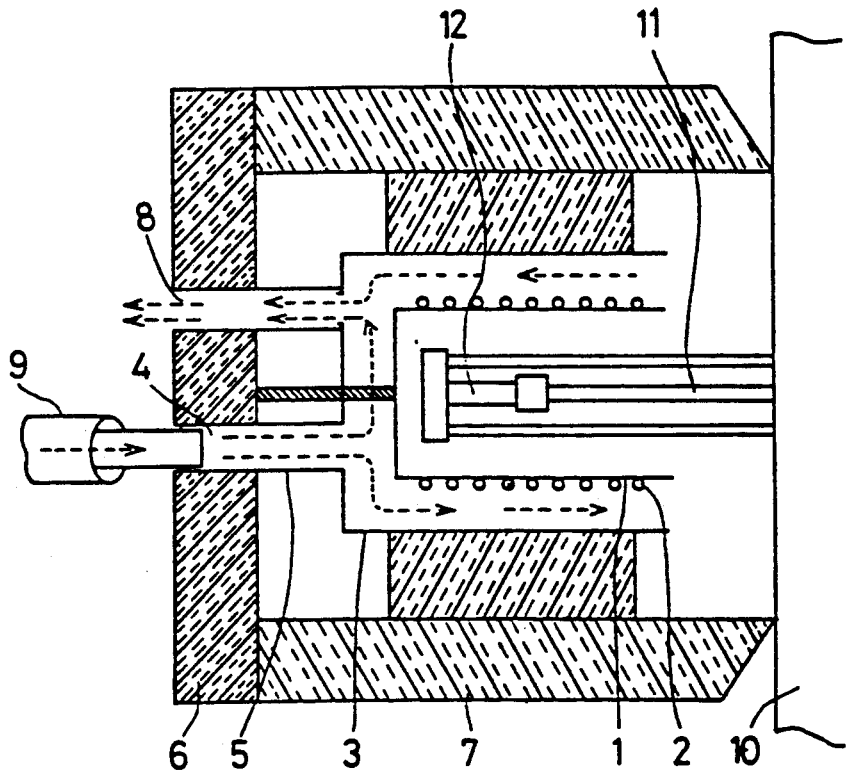
FIG. 1 is a cross sectional view showing an embodiment of a heating furnace according to the present invention.
Figure 2:
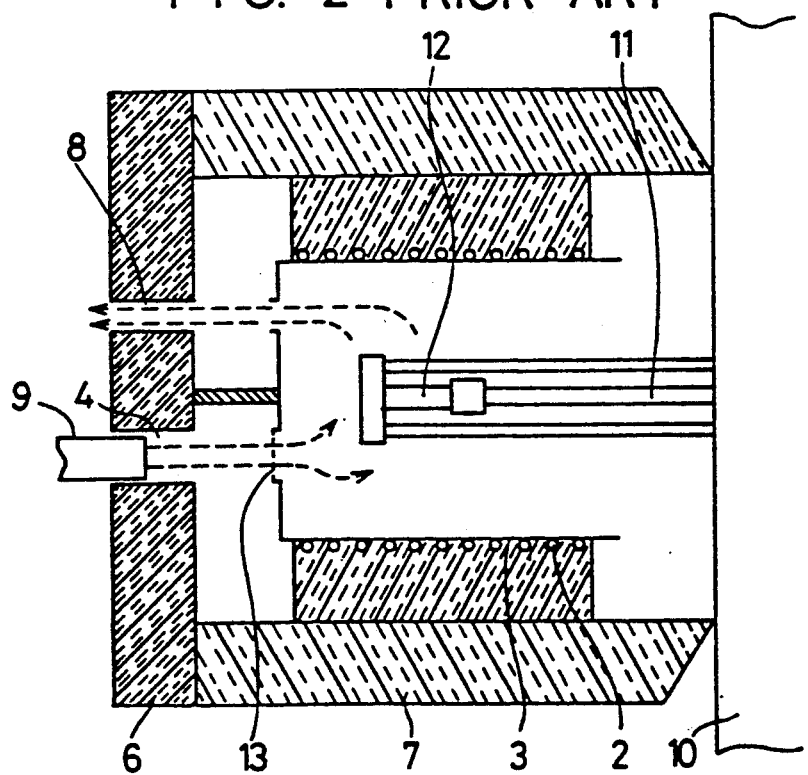
FIG. 2 is a cross sectional view of a conventional heating furnace.

An embodiment of the present invention will now be described with reference to the drawings.

An inner cylinder 1 has a cup-like shape and a heater wire 2 is wound around the outer circumference thereof. An outer cylinder 3 having a cup-like shape similar to that of the inner cylinder 1 is disposed so that the inner cylinder is concentrically positioned inside it, and is fixed inside an adiabatic portion 7 with a screw which is not shown. The outer cylinder 3 has two holes and, at one of the holes, a cylindrical cool air guide pipe 5 is fixed, which is provided in order to introduce cool air drawn in via the cool air introduction hole 4 into the inner cylinder 1 without leakage. At the other hole, an exhaust air guide pipe for ejecting the exhaust air which has been circulated from the cool air introduction pipe 5 is provided in alignment with the position of the exhaust hole 8. A furnace body cover 6 constitues an outer shell of the heating furnace 5 and has a double wall structure in which an adiabatic material for heat insulation is filled. Further, an adiabatic material is filled between the cylinder 3 and the furnace body cover 6 for better heat insulation.

The cooling gas introduced by the liquid nitrogen vaporization type cooling device flows through an adiabatic hose and enters the furnace body via the cool air introduction hole 4. The cool air further flows through the cool air guide pipe 5 and is introduced into the outer cylinder 3 without leakage. The cool air introduced into the outer cylinder 3 is ejected from the exhaust hole 8 after cooling the entire inner cylinder 1 sufficiently.

In this process, the sample 12 fixed on the probe 11 which projects from the body 10 of the device, is not directly exposed to the cool air and, as a result, there is no fluctuation of the temperature in the vicinity of the sample.

In general, when a substance is cooled an error exists between the temperature detected and the acutal temperature due to the thermal capacity of the substance. However, according to the present invention as described above, the linearity of the temperature rise is improved and, as a result, it is possible to correct such an error and the accuracy of measurement is improved.

What is claimed is:

1. In a viscoelasticity measuring apparatus having a furnace for heating a sample whose viscoelasticity is to be measured, the improvement wherein said furnace comprises:
    an internal cylinder having an outer circumference;
    a heater wire wound around the outer circumference of said internal cylinder;
    sample holding means located within said internal cylinder for holding a sample in said internal cylinder to enable the sample to be heated by heat generated by said heater wire;
    an outer cylinder surrounding said internal cylinder to form an annular space with said internal cylinder; and
    a furnace body cover made of a heat insulating material enclosing said outer cylinder, said furnace body cover having a cool gas introduction opening for introducing a cool gas into said space and a cool gas exhaust opening for removing the cool gas from said space.

2. An apparatus as defined in claim 1 wherein said internal cylinder has an axial end which is completely closed.

3. An apparatus as defined in claim 2 further comprising measuring means including said sample holding means for detecting interdependence between the viscoelasticity and the temperature of the sample.

4. An apparatus as defined in claim 3 wherein said measuring means comprise means for detecting the temperature of the sample.

5. An apparatus as defined in claim 1 further comprising means for supplying energy to said heater wire to cause said heater wire to generate sufficient heat to bring the sample to a temperature required to effect a viscoelasticity measurement.

6. An apparatus as defined in claim 1 further comprising a liquid nitrogen vaporization cooling device coupled to supply the cooled gas to said introduction opening.

7. An apparatus as defined in claim 1 further comprising measuring means including said sample holding means for detecting interdependence between the viscoelasticity and the temperature of the sample.

8. An apparatus as defined in claim 7 wherein said measuring comprise means for detecting the temperature of the sample.

* * * * *